United States Patent
Ingimundarson et al.

(10) Patent No.: US 9,375,341 B2
(45) Date of Patent: Jun. 28, 2016

(54) ORTHOPEDIC DEVICE HAVING DETACHABLE COMPONENTS FOR TREATMENT STAGES AND METHOD FOR USING THE SAME

(71) Applicant: OSSUR hf, Reykjavik (IS)

(72) Inventors: Arni Thor Ingimundarson, Gardabaer (IS); Bjorn Omarsson, Reykjavik (IS); Thorleifur Stefansson, Reykjavik (IS); Thorvaldur Ingvarsson, Akureyri (IS)

(73) Assignee: OSSUR hf, Reykjavik (IS)

( * ) Notice: Subject to any disclaimer, the term of this patent is extended or adjusted under 35 U.S.C. 154(b) by 224 days.

(21) Appl. No.: 14/169,786

(22) Filed: Jan. 31, 2014

(65) Prior Publication Data

US 2014/0214016 A1    Jul. 31, 2014

Related U.S. Application Data

(60) Provisional application No. 61/896,375, filed on Oct. 28, 2013, provisional application No. 61/758,964, filed on Jan. 31, 2013.

(51) Int. Cl.
*A61F 5/00* (2006.01)
*A61F 5/01* (2006.01)

(52) U.S. Cl.
CPC .............. *A61F 5/0123* (2013.01); *A61F 5/0125* (2013.01)

(58) Field of Classification Search
CPC ................ A61F 5/0111; A61F 5/0123; A61F 2005/0172; A61F 5/0127; A61F 2005/0137; A61F 2005/0158; A61F 5/01; A61F 2005/0167; A61F 2005/0179; A61F 2220/0008; A61F 2220/0091; A61F 5/0125; A61F 5/013; A61F 5/0102; A61F 5/0106; A61F 50/0123
USPC ................................. 602/16, 20–28; 128/882
See application file for complete search history.

(56) References Cited

U.S. PATENT DOCUMENTS

| 667,768 A | 2/1901 | Puy |
|---|---|---|
| 937,478 A | 10/1909 | Sims |
| 1,153,334 A | 9/1915 | Oswald |
| 1,227,700 A | 5/1917 | Tucker |
| 1,328,541 A | 1/1920 | Palmer |
| 1,510,408 A | 9/1924 | Lychou |
| 1,622,211 A | 3/1927 | Sheehan |
| 2,032,923 A | 3/1936 | Eldridge |

(Continued)

FOREIGN PATENT DOCUMENTS

| DE | 846895 C | 8/1952 |
|---|---|---|
| DE | 100 04 561 A1 | 8/2001 |

(Continued)

OTHER PUBLICATIONS

Advertising Brochure: "Freedom to Perform—Fusion", 5 pages, (2005).

(Continued)

*Primary Examiner* — Michael Brown
(74) *Attorney, Agent, or Firm* — Workman Nydegger

(57) ABSTRACT

An orthopedic device has detachable components for treatment stages of an injury or surgical procedure. The orthopedic device is arranged as a protective functional support for regeneration of knee cartilage after surgical repair procedures, and includes a flexion control kit and a wrap-around liner sleeve.

16 Claims, 11 Drawing Sheets

(56) References Cited

U.S. PATENT DOCUMENTS

| | | | |
|---|---|---|---|
| 2,179,903 A | 11/1939 | Spears |
| 2,467,907 A | 4/1949 | Peckham |
| 2,573,866 A | 11/1951 | Murphy |
| 2,717,841 A | 9/1955 | Biefeld et al. |
| 2,935,065 A | 5/1960 | Homier et al. |
| 3,031,730 A | 5/1962 | Morin |
| 3,046,981 A | 7/1962 | Biggs, Jr. et al. |
| 3,089,486 A | 5/1963 | Pike |
| 3,266,113 A | 8/1966 | Flanagan, Jr. |
| 3,463,147 A | 8/1969 | Stubbs |
| 3,514,313 A | 5/1970 | Martel et al. |
| 3,520,765 A | 7/1970 | Bateman |
| 3,528,412 A | 9/1970 | McDavid |
| 3,561,436 A | 2/1971 | Gaylord, Jr. |
| 3,581,741 A | 6/1971 | Rosman |
| 3,594,863 A | 7/1971 | Erb |
| 3,594,865 A | 7/1971 | Erb |
| 3,742,557 A | 7/1973 | Francois |
| 3,752,619 A | 8/1973 | Menzin et al. |
| 3,758,657 A | 9/1973 | Menzin et al. |
| 3,789,842 A | 2/1974 | Froimson |
| 3,851,357 A | 12/1974 | Ribich et al. |
| 3,877,426 A | 4/1975 | Nirschl |
| 3,916,077 A | 10/1975 | Damrau |
| 3,927,881 A | 12/1975 | Lemelson et al. |
| 3,945,046 A | 3/1976 | Stromgren |
| 3,955,565 A | 5/1976 | Johnson, Jr. |
| 4,193,395 A | 3/1980 | Gruber |
| 4,204,532 A | 5/1980 | Lind et al. |
| 4,240,414 A | 12/1980 | Theisler |
| 4,269,179 A | 5/1981 | Burton et al. |
| 4,269,181 A | 5/1981 | Delannoy |
| 4,275,716 A | 6/1981 | Scott, Jr. |
| 4,280,489 A | 7/1981 | Johnson, Jr. |
| 4,291,072 A | 9/1981 | Barrett et al. |
| 4,296,744 A | 10/1981 | Palumbo |
| 4,336,279 A | 6/1982 | Metzger |
| 4,372,298 A | 2/1983 | Lerman |
| 4,381,768 A | 5/1983 | Erichsen et al. |
| 4,386,723 A | 6/1983 | Mule |
| 4,396,012 A | 8/1983 | Cobiski |
| 4,470,857 A | 9/1984 | Casalou |
| 4,472,461 A | 9/1984 | Johnson |
| 4,506,661 A * | 3/1985 | Foster ................... A61F 5/0123 602/26 |
| 4,528,440 A | 7/1985 | Ishihara |
| 4,554,913 A | 11/1985 | Womack et al. |
| 4,572,170 A | 2/1986 | Cronk et al. |
| 4,617,214 A | 10/1986 | Billarant |
| 4,632,098 A | 12/1986 | Grundei et al. |
| 4,693,921 A | 9/1987 | Billarant et al. |
| D292,529 S | 10/1987 | Saare |
| 4,768,500 A | 9/1988 | Mason et al. |
| 4,775,310 A | 10/1988 | Fischer |
| D298,568 S | 11/1988 | Womack et al. |
| 4,782,605 A | 11/1988 | Cahpnick |
| 4,791,916 A | 12/1988 | Paez |
| 4,794,028 A | 12/1988 | Fischer |
| 4,801,138 A | 1/1989 | Airy et al. |
| 4,802,939 A | 2/1989 | Billarant et al. |
| 4,805,606 A | 2/1989 | McDavid, III |
| 4,854,308 A | 8/1989 | Drillio |
| 4,856,501 A | 8/1989 | Castillo et al. |
| 4,856,502 A | 8/1989 | Ersfeld et al. |
| 4,872,243 A | 10/1989 | Fischer |
| 4,922,929 A | 5/1990 | DeJournett |
| 4,933,035 A | 6/1990 | Billarant et al. |
| 4,953,543 A | 9/1990 | Grim et al. |
| 4,961,544 A | 10/1990 | Bidoia |
| 4,966,133 A | 10/1990 | Kausek |
| 4,989,593 A | 2/1991 | Campagna et al. |
| 4,991,574 A | 2/1991 | Pocknell |
| 4,991,640 A | 2/1991 | Verkindt et al. |
| 5,016,621 A | 5/1991 | Bender |
| 5,018,514 A | 5/1991 | Grood et al. |
| 5,020,196 A | 6/1991 | Panach et al. |
| 5,022,109 A | 6/1991 | Pekar |
| 5,063,916 A | 11/1991 | France et al. |
| 5,067,772 A | 11/1991 | Koa |
| 5,077,870 A | 1/1992 | Melbye et al. |
| 5,085,210 A | 2/1992 | Smith, III |
| 5,112,296 A | 5/1992 | Beard et al. |
| 5,154,682 A | 10/1992 | Kellerman |
| 5,157,813 A | 10/1992 | Carroll |
| 5,181,331 A | 1/1993 | Berger |
| 5,242,379 A | 9/1993 | Harris et al. |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,314,455 A | 5/1994 | Johnson, Jr. et al. |
| 5,316,547 A | 5/1994 | Gildersleeve |
| 5,322,729 A | 6/1994 | Heeter et al. |
| 5,334,135 A | 8/1994 | Grim et al. |
| 5,344,135 A | 9/1994 | Isobe et al. |
| 5,368,549 A | 11/1994 | McVicker |
| 5,383,845 A * | 1/1995 | Nebolon ................. A61F 5/013 602/16 |
| 5,397,296 A | 3/1995 | Sydor et al. |
| 5,415,625 A | 5/1995 | Cassford |
| 5,431,623 A | 7/1995 | Rice |
| 5,437,619 A | 8/1995 | Malewicz et al. |
| 5,445,602 A | 8/1995 | Grim et al. |
| 5,449,341 A | 9/1995 | Harris |
| 5,458,565 A | 10/1995 | Tillinghast, III |
| 5,468,219 A | 11/1995 | Crippen |
| 5,474,524 A | 12/1995 | Carey |
| 5,497,513 A | 3/1996 | Arabeyre et al. |
| 5,500,268 A | 3/1996 | Billarant |
| 5,512,039 A * | 4/1996 | White .................... A61F 5/0106 602/26 |
| 5,514,081 A | 5/1996 | Mann |
| 5,527,269 A | 6/1996 | Reithofer |
| 5,540,982 A | 7/1996 | Scholz et al. |
| 5,542,911 A | 8/1996 | Cassford et al. |
| 5,562,605 A | 10/1996 | Taylor |
| 5,599,288 A | 2/1997 | Shirley et al. |
| 5,614,045 A | 3/1997 | Billarant |
| 5,635,201 A | 6/1997 | Fabo |
| 5,638,588 A | 6/1997 | Jungkind |
| 5,654,070 A | 8/1997 | Billarant |
| 5,656,226 A | 8/1997 | McVicker |
| 5,665,449 A | 9/1997 | Billarant |
| 5,695,452 A | 12/1997 | Grim et al. |
| 5,713,837 A | 2/1998 | Grim et al. |
| D392,877 S | 3/1998 | Eguchi |
| 5,737,854 A | 4/1998 | Sussmann |
| 5,769,808 A | 6/1998 | Matthijs et al. |
| 5,774,902 A | 7/1998 | Gehse |
| 5,795,640 A | 8/1998 | Billarant |
| 5,823,981 A | 10/1998 | Grim et al. |
| 5,840,398 A | 11/1998 | Billarant |
| 5,857,988 A | 1/1999 | Shirley |
| 5,857,989 A | 1/1999 | Smith, III |
| 5,865,776 A | 2/1999 | Springs |
| 5,865,777 A | 2/1999 | Detty |
| 5,865,782 A | 2/1999 | Fareed |
| 5,873,848 A | 2/1999 | Fulkerson |
| 5,891,061 A | 4/1999 | Kaiser |
| 5,900,303 A | 5/1999 | Billarant |
| 5,916,187 A | 6/1999 | Brill |
| 5,948,707 A | 9/1999 | Crawley et al. |
| 5,971,946 A | 10/1999 | Quinn |
| 6,010,474 A | 1/2000 | Wycoki |
| 6,021,780 A | 2/2000 | Darby |
| 6,022,617 A | 2/2000 | Calkins |
| 6,024,712 A | 2/2000 | Iglesias et al. |
| 6,063,048 A | 5/2000 | Bodenschatz et al. |
| 6,110,138 A | 8/2000 | Shirley |
| 6,111,138 A | 8/2000 | Van Wijck et al. |
| 6,142,965 A | 11/2000 | Mathewson |
| 6,152,893 A | 11/2000 | Pigg et al. |
| 6,159,583 A | 12/2000 | Calkins |

(56) References Cited

U.S. PATENT DOCUMENTS

| | | |
|---|---|---|
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,402,713 B1* | 6/2002 | Doyle ................ A61F 5/0123 602/16 |
| 6,405,731 B1 | 6/2002 | Ching |
| 6,413,232 B1 | 7/2002 | Townsend et al. |
| 6,416,074 B1 | 7/2002 | Maravetz et al. |
| 6,461,318 B2 | 10/2002 | Freeman et al. |
| 6,485,776 B2 | 11/2002 | Janusson et al. |
| 6,520,926 B2 | 2/2003 | Hall |
| 6,540,703 B1 | 4/2003 | Lerman |
| 6,540,709 B1 | 4/2003 | Smits |
| 6,543,158 B2 | 4/2003 | Dieckhaus |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 | 5/2004 | Iverson et al. |
| 6,769,155 B2 | 8/2004 | Hess et al. |
| 6,773,411 B1 | 8/2004 | Alvarez |
| 6,861,379 B1 | 3/2005 | Blaszczykiewicz |
| 6,898,804 B2 | 5/2005 | Sandler |
| 6,898,826 B2 | 5/2005 | Draper et al. |
| 6,936,020 B2 | 8/2005 | Davis |
| D519,637 S | 4/2006 | Nordt et al. |
| D519,638 S | 4/2006 | Nordt et al. |
| 7,025,738 B2 | 4/2006 | Hall |
| D520,141 S | 5/2006 | Nordt et al. |
| D521,644 S | 5/2006 | Nordt et al. |
| 7,037,287 B2 | 5/2006 | Cormier et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,303,539 B2 | 12/2007 | Binder et al. |
| 7,367,958 B2 | 5/2008 | McBean et al. |
| 7,448,115 B2 | 11/2008 | Howell et al. |
| 7,762,973 B2 | 7/2010 | Einarsson et al. |
| 7,874,996 B2 | 1/2011 | Weinstein et al. |
| 7,937,973 B2 | 5/2011 | Sorensen et al. |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0132086 A1 | 9/2002 | Su-Tuan |
| 2003/0032907 A1 | 2/2003 | Prahl |
| 2003/0069531 A1 | 4/2003 | Hall |
| 2003/0204156 A1 | 10/2003 | Nelson et al. |
| 2004/0002674 A1 | 1/2004 | Sterling |
| 2004/0054311 A1 | 3/2004 | Sterling |
| 2004/0058102 A1 | 3/2004 | Baychar |
| 2004/0137178 A1 | 7/2004 | Janusson et al. |
| 2004/0137192 A1 | 7/2004 | McVicker |
| 2004/0153016 A1 | 8/2004 | Salmon et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1* | 12/2004 | Lerman ................ A61F 5/0125 602/26 |
| 2005/0038367 A1 | 2/2005 | McCormick et al. |
| 2005/0081339 A1 | 4/2005 | Sakabayashi |
| 2005/0159691 A1 | 7/2005 | Turrini et al. |
| 2005/0160627 A1 | 7/2005 | Dalgaard et al. |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verkade et al. |
| 2006/0090806 A1 | 5/2006 | Friedline et al. |
| 2006/0116619 A1 | 6/2006 | Weinstein et al. |
| 2006/0135902 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0191110 A1 | 8/2006 | Howell et al. |
| 2007/0083136 A1 | 4/2007 | Einarsson |
| 2007/0185425 A1 | 8/2007 | Einarsson et al. |
| 2007/0225824 A1 | 9/2007 | Einarsson |
| 2008/0034459 A1 | 2/2008 | Nordt, III et al. |
| 2008/0229556 A1 | 9/2008 | Hammer |
| 2009/0099562 A1 | 4/2009 | Ingimudarson et al. |
| 2009/0126413 A1 | 5/2009 | Sorensen et al. |
| 2010/0068464 A1 | 3/2010 | Meyer |
| 2010/0125231 A1 | 5/2010 | Knecht |
| 2011/0057466 A1 | 3/2011 | Sachee et al. |
| 2011/0275970 A1* | 11/2011 | Paulos ................ A61F 5/0102 602/16 |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2014/0121579 A1 | 5/2014 | Hinds |

FOREIGN PATENT DOCUMENTS

| | | |
|---|---|---|
| DE | 202004012892 U1 | 10/2004 |
| EP | 0050769 A1 | 5/1985 |
| EP | 0 196 204 A2 | 10/1986 |
| EP | 0611069 A | 8/1994 |
| FR | 2399811 A1 | 3/1979 |
| FR | 2553996 A1 | 5/1985 |
| FR | 2766359 A1 | 1/1999 |
| GB | 2136294 A | 9/1984 |
| GB | 2 455 972 A | 7/2009 |
| WO | 8801855 A1 | 3/1988 |
| WO | 9400082 A1 | 1/1994 |
| WO | 00/49982 A1 | 8/2000 |
| WO | 0070984 A1 | 11/2000 |
| WO | 2006015599 A1 | 2/2006 |
| WO | 2006069221 A2 | 6/2006 |
| WO | 2006069222 A2 | 6/2006 |
| WO | 2008115376 A1 | 9/2008 |
| WO | 2010/117749 A2 | 10/2010 |
| WO | 2011073803 A2 | 6/2011 |

OTHER PUBLICATIONS

Advertising Brochure: "The 9 Innovations of the Axiom Custom Brace", 1 page, Bledose, Medical Technology, Inc. (2005).

International Search Report and Written Opinion from International PCT Application No. PCT/US2014/010410, May 2, 2014.

International Search Report and Written Opinion from International PCT Application No. PCT/US2013/069558, Jul. 3, 2014.

International Search Report and Written Opinion from International PCT Application No. PCT/US2014/010407, Jul. 10, 2014.

International Search Report and Written Opinion from International PCT Application No. PCT/US2014/033266, Jul. 23, 2014.

Article: "An Orthosis for Medial or Lateral Stabilization of Arthritic Knees", by S. Cousins and James Foort, Orthotics and Prosthetics, vol. 29, No. 4, pp. 21-26, Dec. 1975.

Advertising Brochure: "NUKO Camp", 6 pages, Camp International, Inc. Jackson, MI (1984).

(56) References Cited

OTHER PUBLICATIONS

Advertising Brochure: "Lerman Multi-Ligaments Knee Control Orthosis", 2 pages, Zinco Industries, Inc. of Montrose, CA (1985).
In Touch Information on Flexible Polyurethane Foam, vol. 4, No. 3, Jul. 1994, 5 pages.
Advertising Brochure: "The Leader in Knee Motion Management," 8 pages. Donjoy, Carsbad, CA. Feb. 7, 2013.
Advertising Brochure: "The Lenox Hill Lightweight", 1page, Lenox Hill Brace, Inc., New York, NY. Feb. 7, 2013.
Advertising Brochure: "Anderson Knee Stabler", 4 pages, Omni Scientific, Inc. of Lafayette, CA. Feb. 7, 2013.
Advertising Brochure: "OTI Brace", 4 pages, Orthopedic Technology, Inc. of San Leandro, CA. Feb. 7, 2013.
Advertising Brochure: "XCL System", 2 pages, Innovation Sports of Foothill Ranch, CA. Feb. 7, 2013.
Article: "Osteoarthritis of the Knee: An Information Booklet", Arthritis Research Campaign (visited Dec. 14, 2004) http://www.arc.org.uk/about_arth/booklets/6027/6027.htm.
Advertising Brochure: "Fusion", 6 pages, Breg, Inc. of Vista, CA (2005).
Advertising Brochure: "Fusion XT", 2 pages, Breg, Inc. of Vista, CA (2005).
Advertising Brochure: "GII Unloader Select", 2 pagse, Ossur HF of Reykjavik, Iceland (visited Mar. 8, 2005), http://www.ossur.com/pring.asp?pageID=1729.
Advertisement: "Triax", 1 page, Lanxess AG (visited Mar. 8, 2005), http://www.techcenter.lanxess.com/sty/emea/en/products/description/57/index/jsp?print=true&pid=57.
Advertisement: "M2 Inc. Parts Catalog", 3 pages, M2 Inc. of Winooski, VT (visited Mar. 29, 2005), http://www.m2intl.com/medical.MedClsr.htm.
Advertisement: "Axiom", 3 pages, Bledsoe by Medical Technology, Inc. (visited Jun. 15, 2005), http://www.bledsoebrace.com/custom/axiom.asp.
Advertising Brochure: "The Four Axioms of Functional Bracing", 2 pages, Bledsoe by Medical Technology, Inc. (2005).
Reference: "Anatomical Planes", 1 page, (visited Mar. 26, 2005), http://www.spineuniverse.com/displayarticle.phpo/article1023.html.
Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.
Advertisement: "Custom Engineered Fabrics and Products for Advanced High Performance", 1 page, Gehring Textiles (visited Dec. 15, 2005), http://www.gehringtextiles.com/d3.html.
Technical Manual: Bellacure: Restore Your Lifestyle, 10 pages, Bellacure, Inc. (2005).
Technical Manual: "Boa Technology", 3 pages, Boa Technology, Inc. of Steamboat Springs, CO, Feb. 7, 2013.
Advertisement: "Bellacure: The Treatment Device", 6 pages, Bellacure, Inc. (visited Jan. 5, 2006), http://www.bellacure.com/products/index/html.
Advertisement: "Lerman 3-Point Knee Orthosis", 2 pages, Becker Orthopedic of Troy, MI (visited Feb. 26, 2006), http://www.beckerortho.com/knee/3-point/htm.
Article: "Thermoplastic Elastomers TPE, TPR, TPV", 6 pages (visited Mar. 14, 2007), http://www.bpf.co.uk.bpfindustry/plastics_thermplasrubber_TBR.cfm.
PCT International Search Report and Written Opinion Issued on PCT/US08/03237, Jul. 14, 2008, 10 pages.
European Search Report Issued in EP 10 17 2396, Oct. 8, 2010, 5 pages.
European Search Report Issued in EP 08 74 2047, Aug. 1, 2013, 6 pages.
International Search Report and Written Opinion Issued in PCT/IB2010/003540, Oct. 13, 2011, 6 pages.
International Search Report and Written Opinion of the International Searching Authority from International Application No. PCT/US2014/014192, mailed May 20, 2014.

* cited by examiner

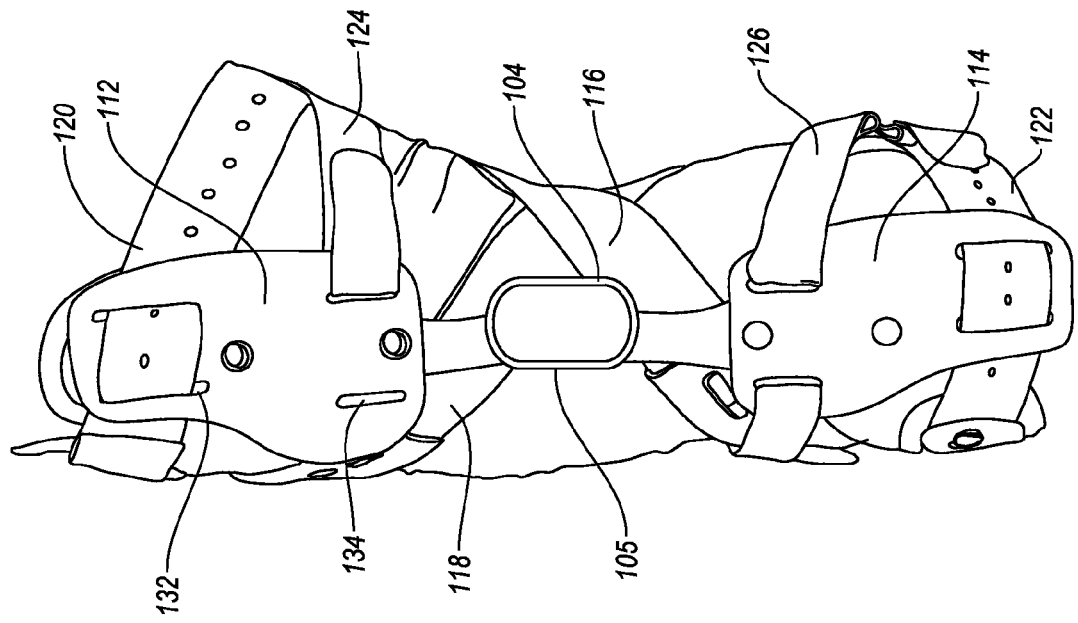
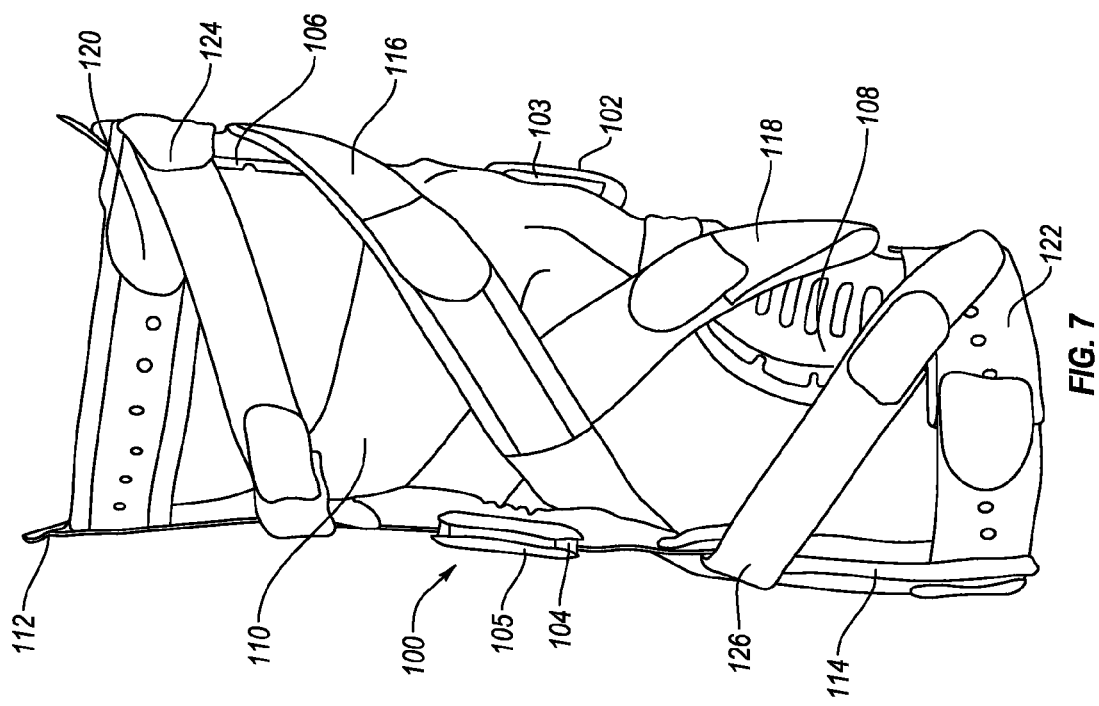

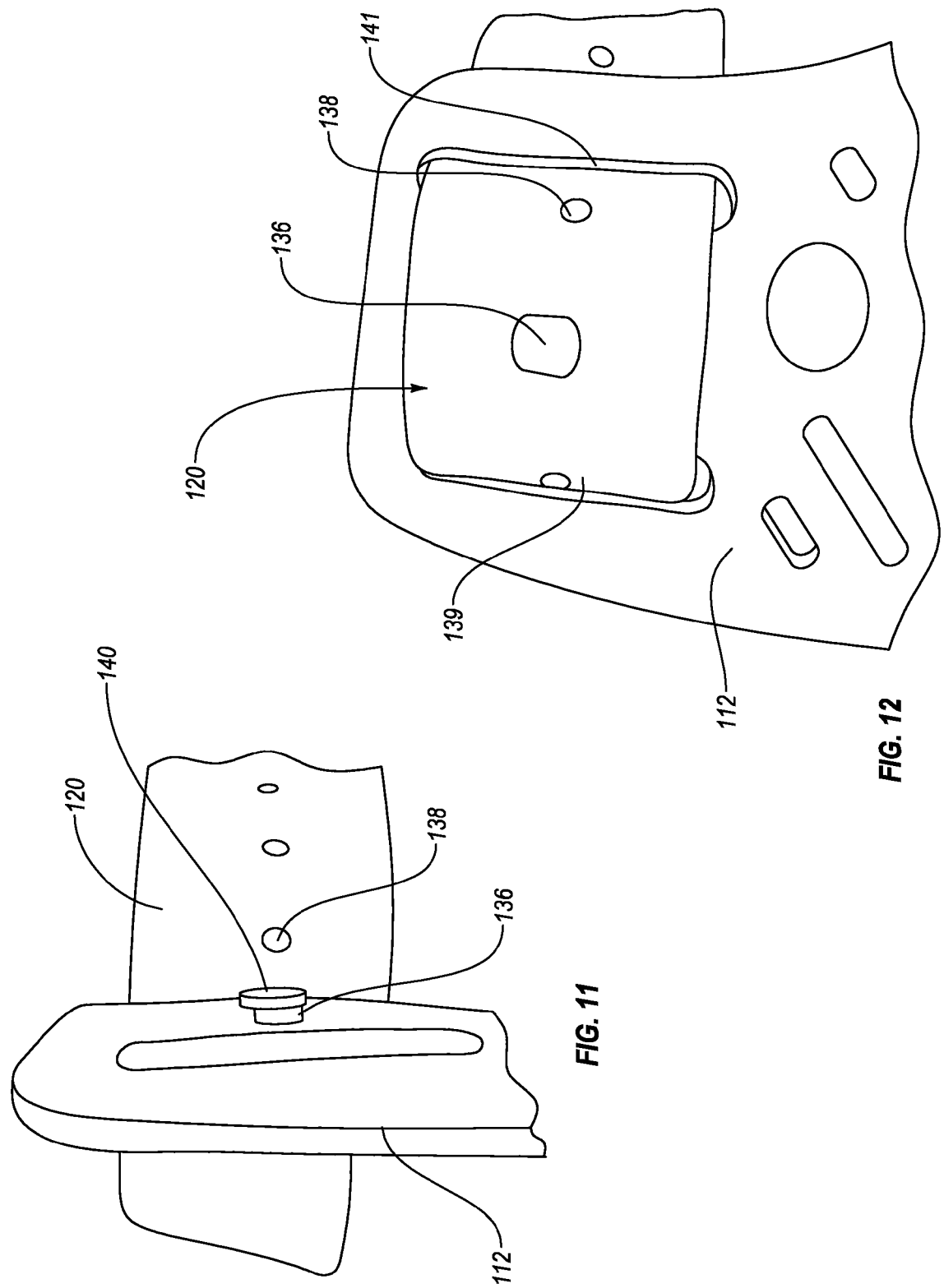

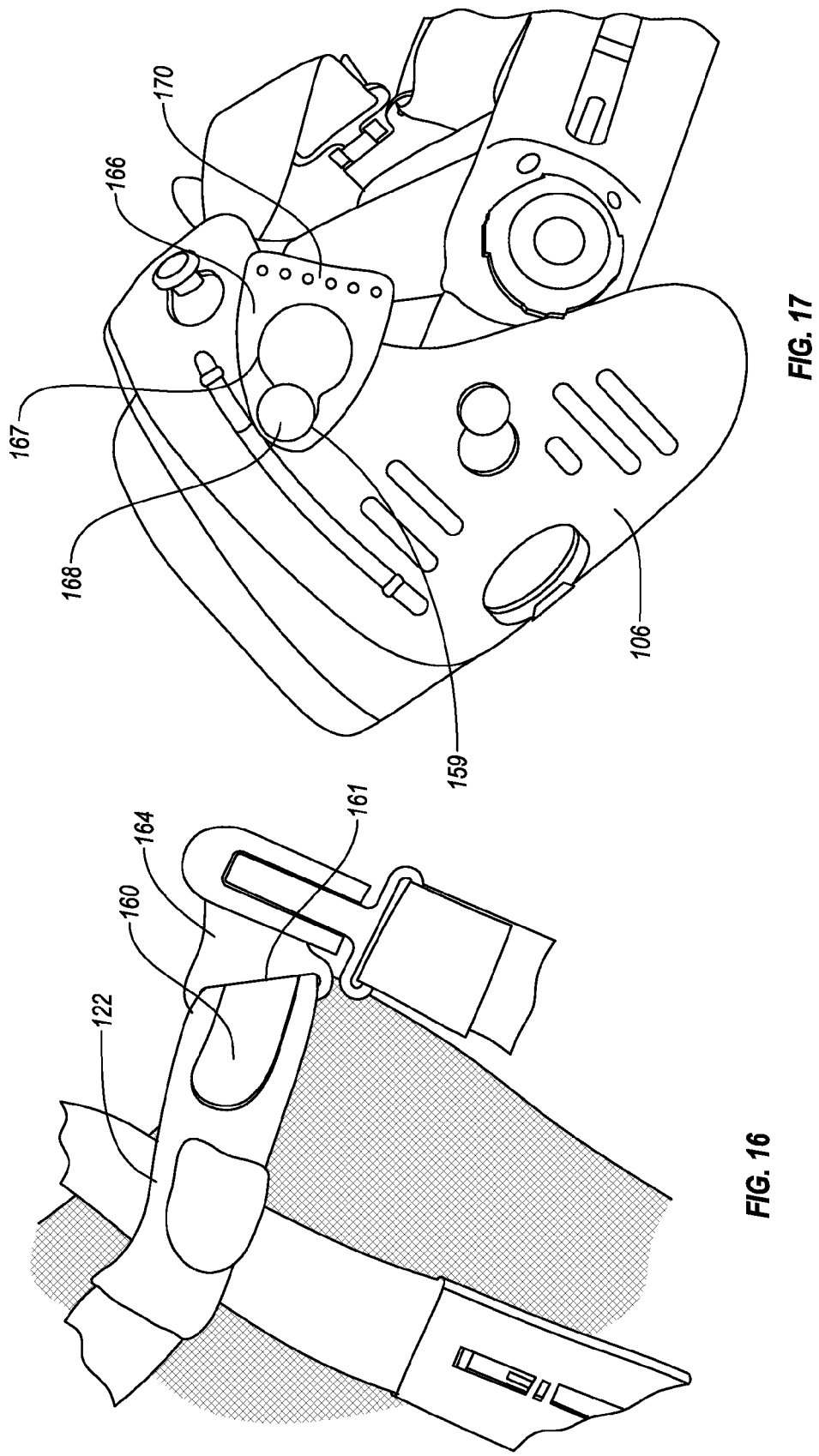

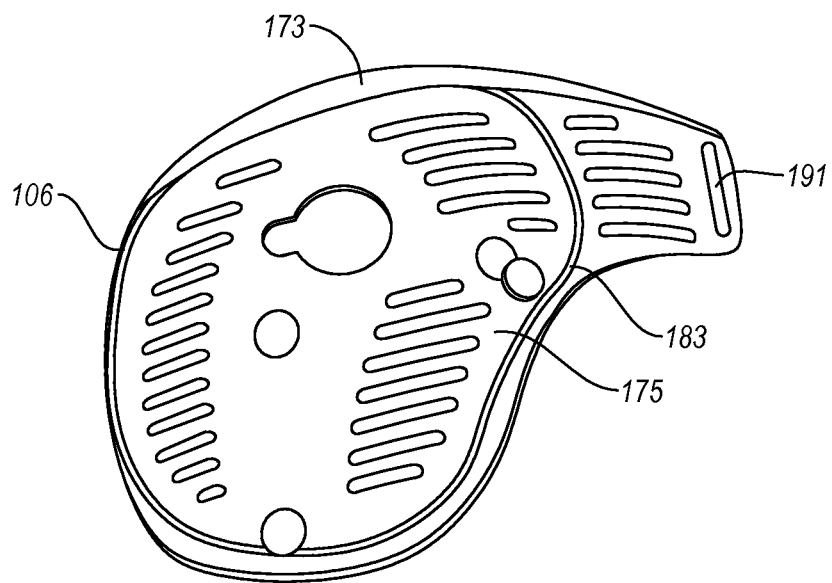
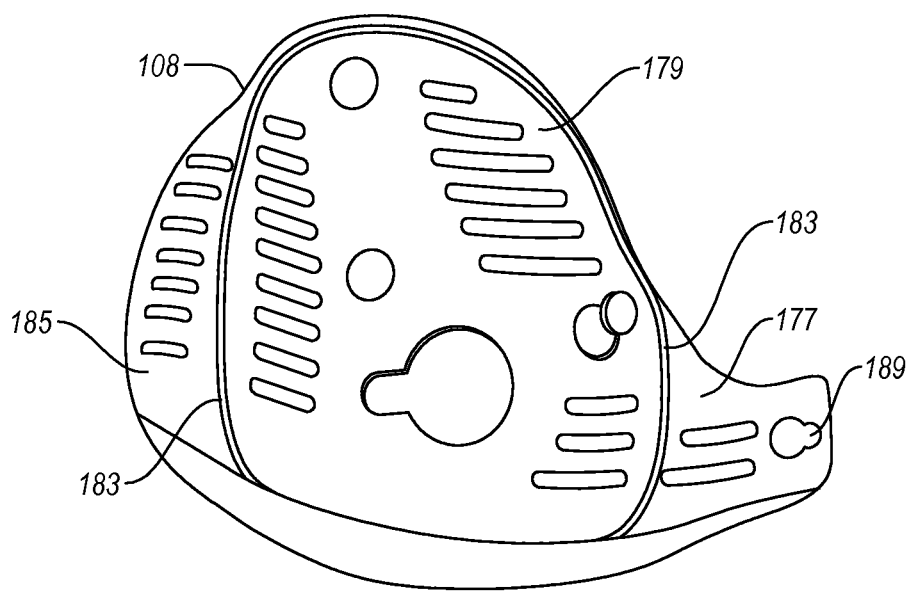
FIG. 19

ORTHOPEDIC DEVICE HAVING DETACHABLE COMPONENTS FOR TREATMENT STAGES AND METHOD FOR USING THE SAME

FIELD OF ART

The embodiments of this disclosure are directed to an orthopedic device, particularly to an orthopedic device having detachable components for treatment stages of an injury or surgical procedure. In a preferred embodiment, the orthopedic device is arranged as a protective functional support for regeneration of knee cartilage after surgical repair procedures.

BACKGROUND

A variety of indications require rehabilitation phases requiring different functions. Most orthopedic devices, inclusive of braces and supports, are arranged for only a single indication and lack the flexibility to be easily modified to the rehabilitation demands of an individual.

Osteoarthritis of the knee is a common cause of musculoskeletal pain and disability of the knee joint. The ends of the femur and tibia are covered with smooth articular cartilage, and meniscal cartilage is located between the ends of the femur and tibia. Osteoarthritis is a slowly progressive disease of the knee joint in which the articular cartilage and subchondral bone gradually wears away, and then progresses into surrounding bone, tissues, synovial fluid. The cartilage may have areas more prone to thinning or complete loss. Isolated loss may result from isolated trauma or may be to chronic wear and tear of the knee.

One of the recognized causes of osteoarthritis initiation is a cartilage lesion from isolated trauma to the knee. Articular cartilage lesions of the knee are a common cause of pain and functional disability. The defects lead to progressive symptoms and degeneration due to either slowness or the inability of the cartilage to heal. Nonoperative rehabilitation is often unsuccessful, and additional treatment may be required to alleviate symptoms since articular cartilage defects do not heal spontaneously. These complications present challenges for individuals who are young and active, and do not otherwise have gross degenerative defects of the knee but have only focal cartilage defects.

Over the last decade, surgeons and researchers have elaborated on surgical cartilage report to treat these lesions. Though these solutions do not perfectly restore articular cartilage, some latest technologies have provided more promising results in repairing cartilage from traumatic injuries or chondropathies (disease of the cartilage). These treatments are particularly targeted at patients who suffer from articular cartilage damage. The treatments provide pain relief while slowing down the progression of damage or considerably delaying joint replacement surgery. Articular cartilage repair treatments help patients return to their original lifestyle by regaining mobility.

Though different articular cartilage procedures differ in surgical techniques, they all share the aim to repair articular cartilage while keeping options open for alternative treatments in the future. One of the promising procedures entails microfracture surgery for repairing articular cartilage defects that involves creating tiny fractures in the underlying bone to cause new cartilage to develop. The technique involves debridement through a calcified cartilage layer followed by perforation of the subchondral bone with surgical awls. A bone marrow clot is formed at the base of the prepared lesion. The clot contains cells that differentiate into cartilage over time (14-18 months) following surgery.

After surgery, the blood clot is delicate and must be protected. The clot takes 8-15 weeks to convert to fibrous tissue and turns into fibrocartilage about 4 months after surgery. Fibrocartilage replaces hyaline cartilage existing at the location prior to the chondral defect and is not as mechanically sound as hyaline cartilage. Because fibrocartilage is more dense and less durable to withstand daily activities, and there is a higher risk of breaking down than hyaline cartilage.

In view of these factors, rehabilitation from microfracture surgery may last multiple months as the fibrocartilage forms. Rehabilitation includes several phases depending on the level of healing: (1) non-weightbearing (weeks 0-6), (2) progressive strengthening and loading (weeks 6-12), (3) neuromuscular retraining (weeks 12-24), and (4) return to activity (weeks 24 and beyond). Within the retraining and return to activity protocols, different sport levels include: low-impact sports (2-3 months), (5) higher impact sports (4-5 months), and (6) high-impact pivotal sports (6-8 months).

Rehabilitation following any cartilage repair procedure is paramount for success of any cartilage resurfacing technique. Rehabilitation is long and demanding. The main reason for the duration of rehabilitation is the cartilage cells must adapt and mature into repair tissue. Cartilage is a slow adapting substance, and where muscle takes approximately 35 weeks to fully adapt itself, cartilage only undergoes 75% adaptation in 2 years. If rehabilitation is too short, the cartilage repair might be under too much stress, causing the repair to fail.

An unloading brace of the type described in U.S. Pat. No. 7,198,610 may be used during the partial weightbearing phase and onwards until full recovery has been achieved. The unloading brace reduces the load applied to the clot and mitigates or prevents damage as the clot coverts to fibrous tissue. While crutches may likewise reduce weightbearing, an unloading brace permits the individual to use the affected limb, which at least helps keep the joint flexible, increases the range of motion, and prevents surrounding muscles from atrophy.

An unloading brace applies a gentle force design to reduce the pressure on the affected part of the knee, particularly where the lesion is formed, resulting in reduction in pain. The force unloads pressure on the affected part of the knee and orients the knee so the affected part is not further aggravated.

There is evidence that cartilage damage in chondral lesions may eventually lead to developing osteoarthritis, regardless of the surgical treatment. There is some indication for continued an unloading brace, even after the clot has fully developed into fibrocartilage, particularly in view of its inherent weakness compared to hyaline cartilage.

From the foregoing, there is a need for an orthopedic device arranged for providing protective support for regeneration of knee cartilage after surgical repair procedures. The need is further accentuated by providing a solution adaptable for different treatment stages during the healing process and rehabilitation of cartilage repair.

SUMMARY

Embodiments of the disclosure are directed to an orthopedic device having detachable components for treatment stages and methods for using the same. Taking microfracture as an example, the orthopedic device has components that can be added or removed over rehabilitation phases following surgery and used for continued use after the rehabilitation phases are complete.

The orthopedic device can be used for articular cartilage defect repair needing unicompartmental load reduction or range of movement restriction. Various embodiments may be employed for treating cartilage knee trauma benefiting from unloading or movement restriction and pain relief. Embodiments may treat unicompartmental knee conditions requiring unloading, movement restriction and pain relief such as for meniscal repair, avascular necrosis, and condylar bone marrow lesions.

In an embodiment of the disclosure, the orthopedic device includes a frame including first or upper and second or lower portions or shells, a first hinge assembly permanently secured to and connecting the first and second frame portions, and a second hinge assembly detachably connected to the first and second frame portions. The second hinge assembly or flexion control assembly may be used in early rehabilitation phases requiring significant stability and may be removed in later phases when only a single hinge assembly will suffice for a lower-profile orthopedic device.

The shells of the frame are preferably low profile and thin to yield over portions of a user's leg. The shells may define a plurality of elongate openings extending laterally relative to a user's leg to facilitate bending over the user's leg. The elongate openings allow for ventilation over the user's leg and preferably serve not to bulge significantly from a user's leg, but rather closely embrace a user's leg despite volume changes of a user's leg over rehabilitation stages and during gait. The shells preferably have a wide profile to snugly secure to a user's leg while yielding to movement of a user's leg and distributing pressure over the leg due to tightening of the shells by straps connected thereto.

In a variation of the shells, the shells include regions having different thickness in order provide sufficient structural support while adding the requisite flexibility to closely embrace the leg depending on any volume changes. At least one of the shells may have a thickened region corresponding to a side portion upon which a strut and hinge assembly secures to the frames. A thinned anterior region preferably extends from the thickened region, such as over the anterior upper and lower leg portions. A thinned peripheral region may surround the thickened region, and may either be thicker or thinner than the thinned anterior region. The shells are preferably formed from the same material and the thinned and thickened regions are continuously formed without interruption of the same material or from region to region. An example is that each shell may be injection molded by a polymeric material and formed in a same mold having both the thickened and thinned regions.

The thinned anterior region may include a slot at a free end portion for receiving a corresponding suspension strap. In this manner, rather than using a buckle or strap tab, the slot reduces pivoting of the free end portion of the shell, especially with the upper or thigh shell. The thinned anterior region with the slot allows the suspension strap to tightly secure against the thigh of a user to allow the shell at least at the thinned anterior region to closely follow the contour of a user's leg through volume changes.

The second hinge assembly or flexion control kit provides improved modular flexion control for patients lacking such control. It can be added and removed from the orthopedic device without an effect on the unloading function. Once installed, it does not hinder donning or doffing of the orthopedic device from the patient. The second hinge assembly may have first and second struts connected to one another by a hinge that may be similar to the first hinge assembly. The second hinge assembly may also have a support mounted at and extending from a first end of the first strut, such as upper and lower frame components adapted to embrace the leg by distributing pressure over a user's leg.

Suspension straps may be secured to opposed sides of the first and second frame portions. The second hinge assembly may detachably secure to the suspension strap. The second hinge assembly may include a fastener element directly securable to the suspension strap to prevent migration of the suspension strap relative to the second hinge assembly. The second hinge assembly may include upper and lower slots each defining a pin arranged to extend into openings formed by a corresponding suspension strap to maintain the second hinge assembly with the first hinge assembly.

A stability strap may be generally arranged to form a circumferential loop about the first and second hinge assemblies. Upper and lower stability straps may be located adjacent to and above and below, respectively, a knee or other joint. The suspension strap is secured at or adjacent a first end portion of the first and second strut assemblies. The stability strap is mounted below the first end portion of the first and second strut assemblies. The suspension strap and the stability strap extend over the first and second strut assemblies.

A force or cartilage protection strap may be spiraled between and connect to the first and second frame portions. The cartilage protection strap may extend between first and second suspension straps, and extend over the stability straps in areas outside of unloading the joint. The cartilage protection strap is arranged to provide greater range of motion, and to create a snug fit when the knee if flexed.

A wrap-around liner sleeve may extend between and beyond the length of the first and second strut assemblies with the frame extending over the liner sleeve. The liner sleeve is arranged to increase comfort, and reduce irritation over the popliteal area of a user's knee. The liner sleeve is arranged for easy donning, and is formed from a breathable material. The liner sleeve may include a frictional substance to provide suspension on a user's leg and minimize migration during user, and other substances or surfaces formed by a layer or layers for providing enhanced comfort to the user.

The liner sleeve defines an anterior opening allowing for exposure of a user's knee at incision sites, which reduces or prevents irritation and interference from bandaging. The opening of the liner sleeve at the knee, which would otherwise undergo the greatest amount of tension in material of the sleeve, improves the fit and decreases bunching of the sleeve.

The liner sleeve is optionally secured to the orthopedic device, and includes means for easily attaching and removing from the orthopedic device. In an embodiment, the liner sleeve includes upper and lower padded regions corresponding to the upper and lower frame components. A first section of elastic and breathable material extends between the upper and lower padded regions and corresponds generally to the first hinge assembly. A second section of elastic and breathable material extends from the upper and lower padded regions and is arranged for wrapping about the leg. The second section of material includes fasteners at upper and lower ends for attaching to upper and lower buckle assemblies, respectively, carrying certain ends of the suspensions straps and the cartilage protection straps so the liner sleeve can be wrapped about a user's leg simultaneously with attachment of the buckle assemblies to the upper and lower shells.

Various methods may use the orthopedic device during rehabilitation phases. The methods may include applying and maintaining a force with the strap on a knee at a side of a knee opposite repairing cartilage, maintaining a selected range of motion of the knee by a range of motion hinge of the orthopedic device by adjusting flexion and extension stops on the range of motion hinge, providing stability to the knee by lateral stability straps connected to the orthopedic device and circumferentially extending at adjacent locations above and below the knee.

Another method may also include steps for permanently securing the first hinge assembly to the first and second portions and detachably mounting the second hinge assembly to the first and second portions after certain rehabilitation phases are completed. Yet another method may entail attaching and removing the liner sleeve from the orthopedic device, and donning and doffing the liner sleeve when already attached to the orthopedic device, particularly by securing certain ends of the liner sleeve to buckle assemblies quickly detachable from and attachable to the frame of the orthopedic device.

The numerous advantages, features, and functions of the embodiments will become readily apparent and better understood in view of the following description and accompanying drawings. The following description is not intended to limit the scope of the orthopedic device, but instead merely provides exemplary embodiments for ease of understanding.

BRIEF DESCRIPTION OF THE DRAWINGS

These and other features, aspects, and advantages of the present disclosure will become better understood regarding the following description, appended claims, and accompanying drawings.

FIG. 7 is a front elevational view depicting another embodiment of the orthopedic device of FIG. 1.

FIG. 8 is a side elevational view depicting the orthopedic device of FIG. 7.

FIG. 11 is a detailed sectional view showing the attachment of a suspension strap to a second strut assembly.

FIG. 12 is another detailed sectional view showing the suspension strap attached to the second strut assembly of FIG. 11.

FIG. 16 is a detailed sectional view showing attachment of a strap tab of the liner sleeve to a buckle assembly.

FIG. 17 is a detailed sectional view showing a variation of a strap tab for attachment to the orthopedic device of FIG. 7.

FIG. 19 is a perspective view of upper and lower shells for use in the orthopedic device.

DETAILED DESCRIPTION OF VARIOUS EMBODIMENTS

A. Overview

Figure 2:
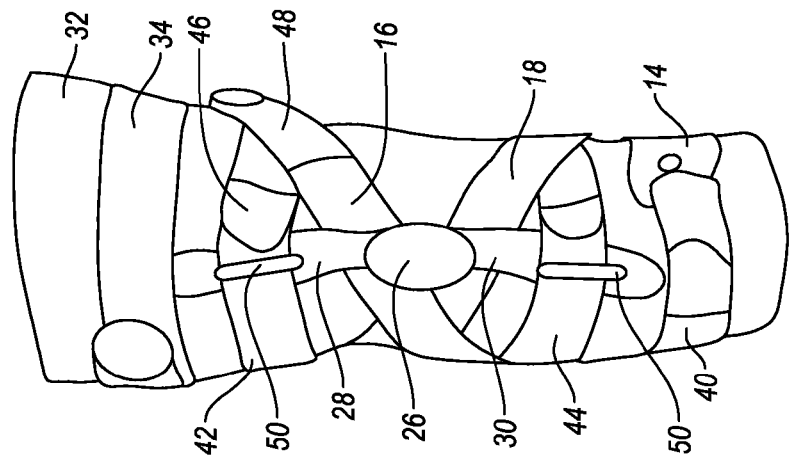
FIG. 2 is a side elevational view depicting the embodiment of FIG. 1.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined herein to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. §112, paragraph 6.

B. Definitions

For ease of understanding the disclosed embodiments of an orthopedic device, the anterior and posterior portions of the orthopedic device may be described independently. Anterior and posterior portions of the orthopedic device function together to support and stabilize anatomical portions of the user of the device.

For further ease of understanding the embodiments of an orthopedic device as disclosed, a description of a few terms, when used, is necessary. As used, the term "proximal" has its ordinary meaning and refers to a location situated next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Lastly, the term "anterior" has its ordinary meaning and refers to a location ahead of or to the front of another location.

The terms "rigid" and "flexible" may distinguish characteristics of portions of certain features of the orthopedic device. The term "rigid" should denote an element of the device is generally devoid of flexibility. Within the context of frame or support members or shells that are "rigid," it is intended to indicate that they do not lose their overall shape when force is applied, and they may break if bent with sufficient force. The term "flexible" should denote that features are capable of repeated bending such that the features may be bent into retained shapes or the features do not retain a general shape, but continuously deform when force is applied.

As for the term "semi-rigid," this term is used to connote properties of support members or shells that provide support and are free-standing; however such support members or shells may have some degree of flexibility or resiliency.

C. Description of Orthopedic Device Embodiments

Figure 1:
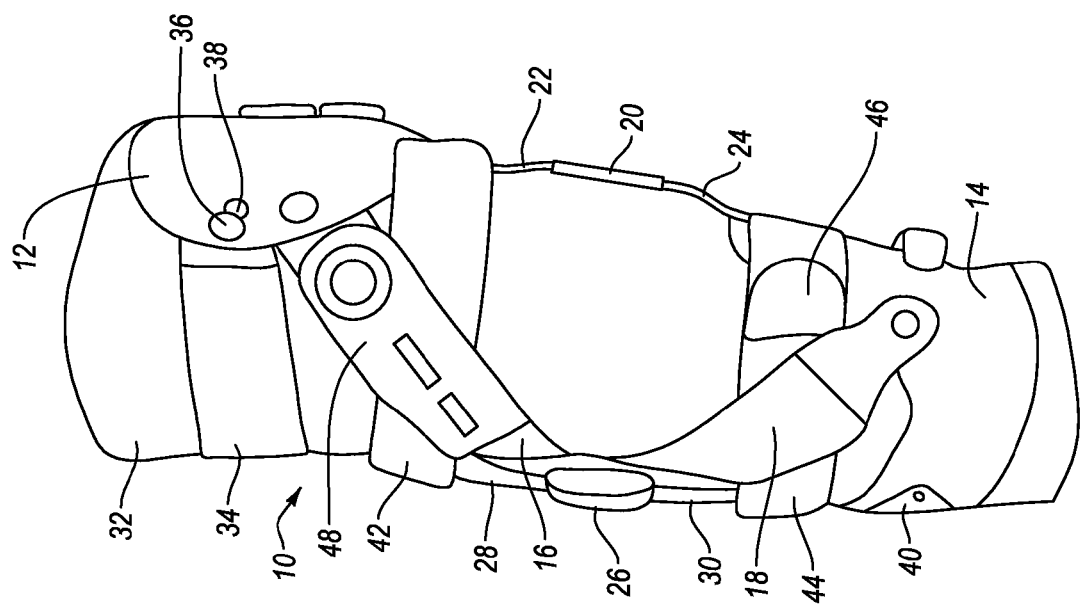
FIG. 1 is a front elevational view depicting an embodiment of the orthopedic device.
Figure 3:
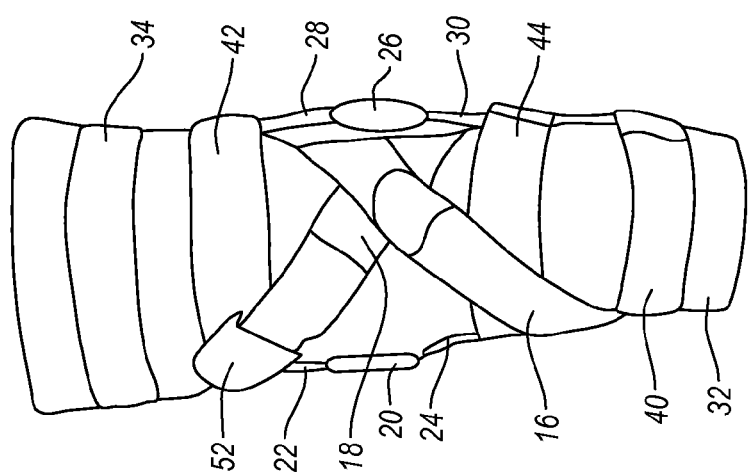
FIG. 3 is a rear elevational view depicting the embodiment of FIG. 1.

Referring to the embodiment of FIGS. 1-3, an orthopedic device 10 has removable components in combination with permanent components adapted for different treatment stages in rehabilitation of an injury, surgery, or defect. The orthopedic device is described as an unloading-type brace, as taught in U.S. Pat. No. 7,198,610, granted Apr. 3, 2007 and incorporated herein by reference, however, the orthopedic device may be of any device directed to braces and supports.

As illustrated, the orthopedic device 10 has a frame including upper and lower frame components 12, 14 located above and below the knee, respectively. As with unloading-type braces, the device 10 has first and second dynamic force straps 16, 18, adapted to relieve a compartment of the knee.

The orthopedic device preferably uses cartilage protection straps having progressive loading with elastic features as dynamic force straps. Embodiments of cartilage protection straps having elastic features are described in greater detail in U.S. patent application Ser. No. 14/148,981, filed on Jan. 7, 2014, incorporated herein by reference. The cartilage protection straps are distinguishable over the conventional dynamic force straps in that due to their elastic segments, the cartilage protection straps can create a greater moment generated by the strap over a wider degree of knee flexion.

Figure 20:
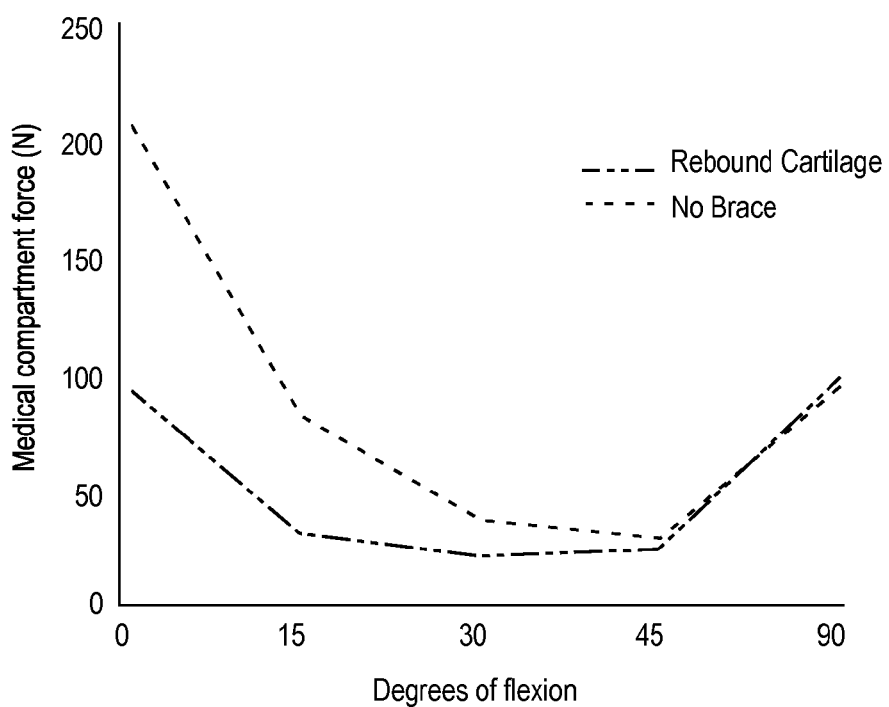
FIG. 20 is a graph showing the moment generated by a compressive force strap versus a moment generated by a conventional force strap.

As shown in FIG. 20, the moment generated by the cartilage protection strap is greater generally just after flexion occurs and continues generally as flexion of the knee progresses. The results obtained by FIG. 20 particularly refer to the embodiments described herein, and have the features described herein. Some of the wider range of protection obtained by the embodiments is due in part by the substantial flexibility of the frame components, and the strapping systems described herein.

Alternatively, a conventional dynamic force strap generally inelastic, adjustable and tensionable as disclosed by U.S. Pat. No. 7,198,610. The disclosure refers interchangeably to force straps for both force straps having elastic features and the conventional force straps, and to the embodiments of the disclosure as cartilage protection straps.

A tensioning or dosing device 48, 52 may be provided to allow for incremental tensioning of the force straps by a controlled, predetermined manner. An example of a tensioning or dosing device may be found in at least U.S. Pat. No. 7,198,610 or U.S. application Ser. No. 13/739,491, filed on Jan. 11, 2013, and published on Jul. 18, 2013 as U.S. published application No. 2013/0184628, and incorporated by reference.

According to the embodiments shown, the tensioning device has a flexible sleeve covering at least in part the strap and internal components of the tensioning device. The sleeve is arranged to substantially flex to closely conform to the shape of a user's leg through tensioning of the force straps and volume changes of a user's leg. The flexibility may be obtained by making the sleeve thin and/or including slots to facilitate twisting and bending.

A first hinge assembly is on the medial side of the leg and has a hinge 20 and upper and lower strut segments 22, 24 that secure to the upper and lower frame components 12, 14, respectively. The first hinge assembly is preferably permanently secured to the upper and lower frame components 12, 14. According to the illustrated embodiment, the force straps 16, 18 are oriented to relieve compartmental arthritis on the lateral side of the leg, and exert forces toward the medial side of the device, which are resisted in part by the first hinge assembly.

A second hinge assembly or flexion control kit is detachably secured to the lateral side of the leg, and has a hinge 26 and upper and lower strut segments 28, 30. The second hinge assembly can be secured to the device 10, but is detachable when it is not required to include the enhanced stability that the second hinge assembly provides.

A liner sleeve 32 extends along the leg surface, and preferably compresses the leg just after surgery and in the early months of rehabilitation. The liner sleeve 32 may be secured to the frame so it is unitary with the orthopedic device, or may be provided separately from the frame. In an alternative configuration, the liner sleeve serves as an interface upon which the various straps and the frame of the orthopedic device secure, particularly if the leg and knee are tender from recent surgery.

The device 10 has an upper suspension strap 34 that secures to opposed sides of the upper frame 12 and is adjustable to accommodate the user's leg. The suspension strap 34 extends laterally over the thigh of the user and prevents migration of the device on the leg. The upper suspension strap 34 has a first end including a mount 38, such as a hook or pin arranged to engage a slot 36 formed by the upper frame 12 enabling a quick connect/disconnect of the suspension strap 34 on the brace. A second end of the upper suspension strap 34 is likewise removably secured to the upper frame 12 by a buckle or other type of mount.

The device 10 has a lower suspension strap 40 secured to the lower frame 14 in a manner similar to the upper suspension strap 34. The upper and lower suspension straps 34, 40, are preferably at upper and lower end portions of the device. The suspension straps are tensionable and suspend the brace on the leg of the user.

Upper and lower range of motion (ROM) or stability straps 42, 44 are provided proximate and adjacent to a knee of the user. The ROM straps 42, 44 are located above and below the hinges 20, 26, and provide additional stability on the leg of the user in areas defined between the suspension straps. The ROM straps 42, 44 are proximate and adjacent to the knee to more closely secure the knee to the movement of the hinges 20, 26. Each of the ROM straps 42, 44 includes a tab for adjusting the tension in the strap.

The ROM straps 42, 44 are arranged to circumferentially encircle the leg and extend over the struts of the hinge assemblies to urge these struts to closely conform to the knee in the region above and below the knee. The force straps are configured to extend over the ROM straps 42, 44 so the force straps can be adjusted in tension when the brace is worn. Under normal circumstances, the ROM straps are only tensioned once the device is donned.

The ROM straps 42, 44 are removably secured to the device in part because they may only be required in early phases of rehabilitation when close control of the range of motion of the knee is required. A strap retainer 50 is on the struts of the strut assemblies, and permits easy installation of the straps to the device, depending on the need for their enhanced support.

Figure 4:
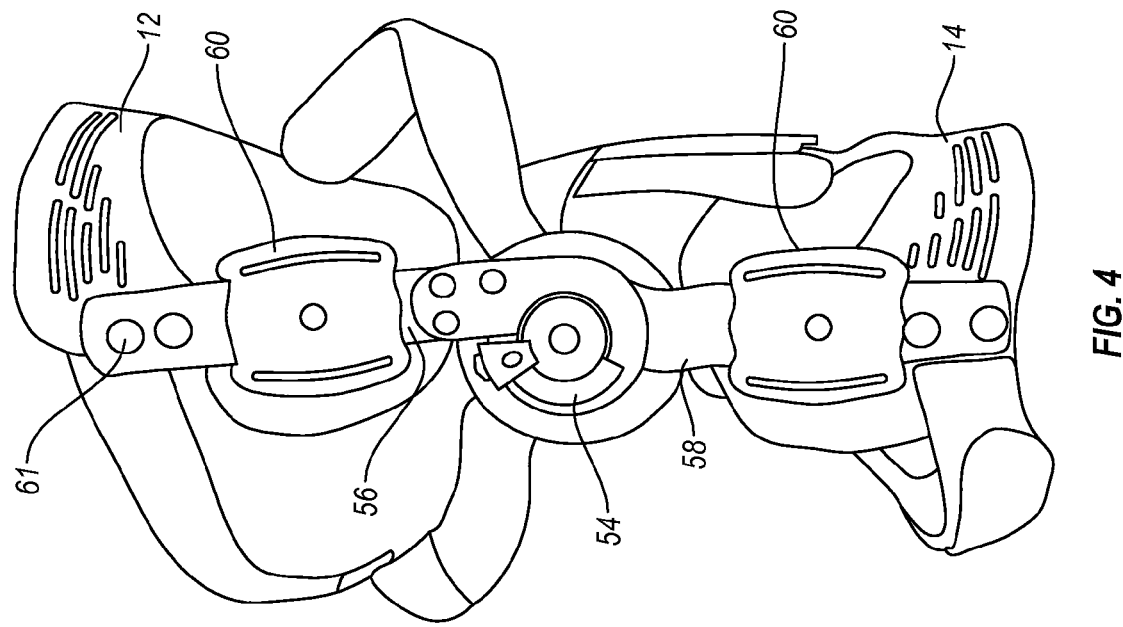
FIG. 4 is a perspective view showing a variation of the embodiment of FIG. 1.

As shown in FIG. 4, at least one of the hinge assemblies, preferably the second hinge assembly, has a range of motion (ROM) hinge 54 including flexion and extension stops. An example of a ROM hinge is found in U.S. Pat. No. 7,037,287. The strut assembly including the ROM hinge 54 may include upper and lower struts 56, 58, forming loops 60 that permit attachment of the ROM straps. The loops 60 may be formed by the upper and lower struts 56, 58, or may be supported by a liner sleeve attached to the upper and lower struts 56, 58.

The upper and lower struts 56, 58 may be secured to the upper and lower frames 12, 14, by fasteners 61. The fasteners 61 may permanently secure the upper and lower struts 56, 58 to the frames, such as by rivets or other suitable fasteners, or they may detachably secure the upper and lower struts 56, 58 to the frame, such as by snaps, hook and loop, and other suitable fasteners permitting a detachable connection. In this variation, the frame must extend sufficiently over to the side for the upper and lower struts 56, 58 to connect.

Figure 6:
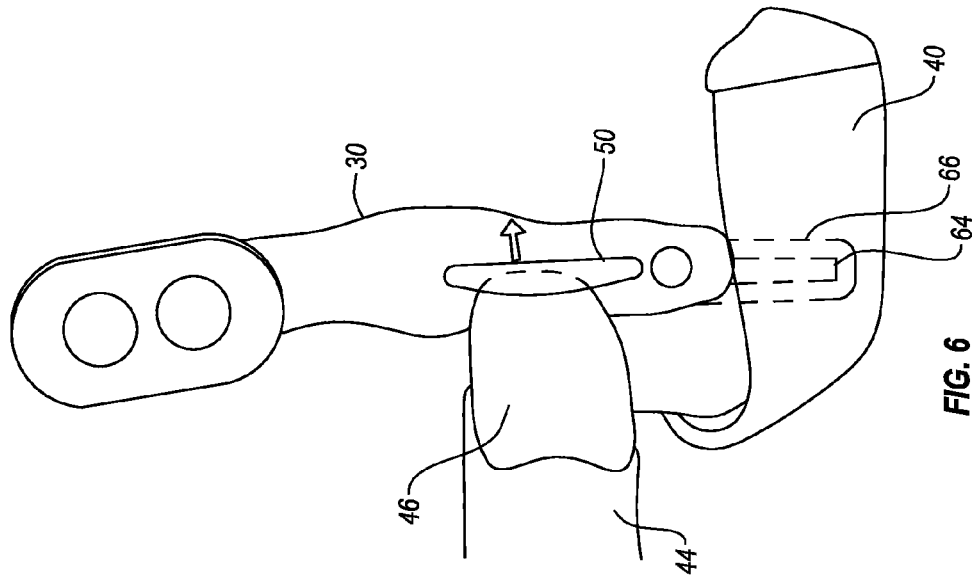
FIG. 6 is another schematic detail view showing the strut assembly in the embodiment of FIG. 1.
Figure 5:
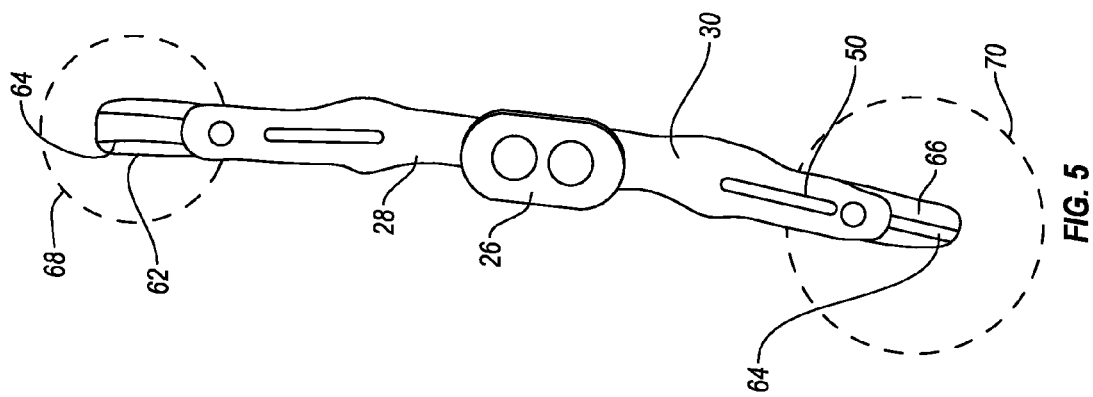
FIG. 5 is a schematic detail view showing a detachable strut assembly in the embodiment of FIG. 1.

FIGS. 5 and 6 depict a variation of the second hinge assembly of FIGS. 1-3. The upper and lower struts 28, 30 each include a support 62, 66 adapted to detachably secure to the device 10. In this variation, the support 62, 66 defines an extension adapted to secure at least to the suspension straps by a connection 64. The connection 64 may be formed by a hook and loop fastener that engages the suspension straps, or alternatively may define a loop through which the suspension straps extend. The support should be sufficiently strong to engage the suspension straps and endure the rigors of maintaining the hinge assembly on the orthopedic device. In an alternative embodiment, the support 68, 70, may be significantly larger to embrace a larger portion of the user's leg and provide more stability As the second hinge assembly is easily removable from the device 10, the struts may define a strap retainer that can be used without making the brace bulky and obtrusive, particularly when there are no ROM straps.

FIG. 6 illustrates a strap retainer 50 defined as a flexible loop extending from the lower strut 30 and enabling the strap tab 46 and ROM strap 44 to extend therethrough. The strap retainer 50 may be formed from a textile, polymer or other suitable flexible material available to support the ROM strap. It is preferable that the strap retainer 50 is inelastic, but it may be likewise elastic.

The adaptability of the second hinge assembly and the strap retainers allow the device to be converted to a significantly stable and tightly secured brace for recent post-surgical rehabilitation, particularly involving microfracture. Over rehabilitation, the liner sleeve, the ROM straps, and the second hinge assembly may be removed as less stability and range of motion control is needed. Even after rehabilitation is ended, the device can be converted into a conventional unloading brace to treat or prevent ongoing symptoms of the knee.

Referring to the embodiment of FIGS. 7 and 8, the orthopedic device 100 includes first and second strut assemblies 102, 104, each carrying upper and lower frame components 106, 112, 108, 114, respectively. A liner 110 is secured between the first and second strut assemblies 102, 104. Force straps 116, 118 spirally depend and connect to the upper and lower frame components 106, 108 of the first strut assembly 102. Suspension straps 120, 122 connect to the upper and lower frame components 106, 112, 108, 114, respectively. Upper and lower range of motion (ROM) or stability straps 124, 126, connect to opposed corresponding upper and lower frame components 106, 112, 108, 114 by a retainer such as a slot 134 formed in the frame components, fastening means such as hook and loop, or other suitable means.

The second strut assembly 104 defines a flexion control kit removably secured to the orthopedic device 100. The ROM straps 124, 126, spiral upwardly and downwardly, respectively, from the upper and lower frame components 112, 114, of the second strut assembly 104 to the upper and lower frame components 106, 108.

Figure 10:
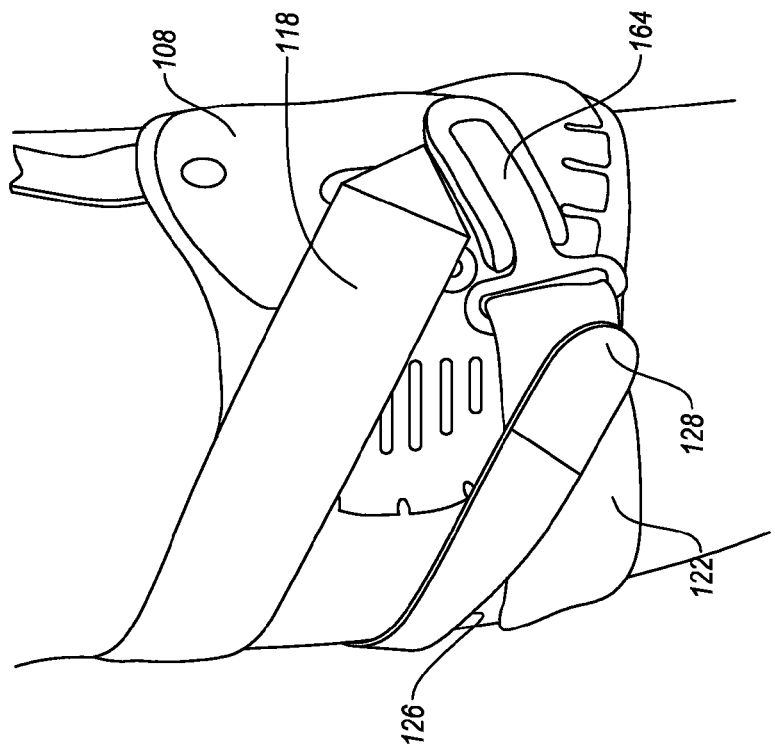
FIG. 10 is another rear sectional view showing the range of motion strap attached to the suspension strap of FIG. 9.
Figure 9:
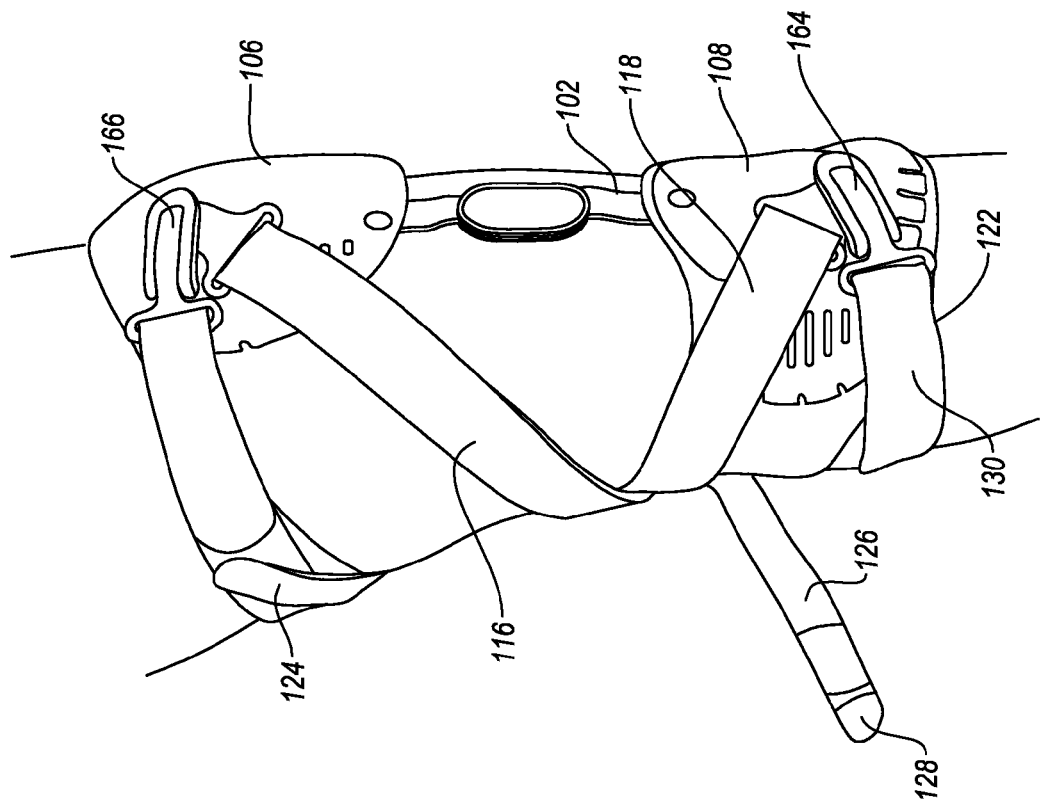
FIG. 9 is a detailed rear sectional view showing the attachment of a range of motion strap to a suspension strap.

As shown in FIGS. 9 and 10, a tab 128 extending from the ROM strap 126, can secure to the surface 130 of the suspension strap 124. The ROM straps may likewise secure to the surface of the force straps. The tab 128 may removably secure to the end of the ROM straps, and possess an alligator flap-type, or single flap hook attachment to the end of the ROM straps. The ROM straps may be trimmed to an appropriate length. By securing the ROM straps to the corresponding suspension straps, the ROM straps can be loosened from the user when buckle assemblies 164 carrying both the force straps and suspension straps are loosened from the respective upper and lower frame components. Examples of the buckle assemblies are found in U.S. Pat. No. 7,198,610.

The first and second strut assemblies each include hinges, which may be generally the same, and strut elements extending from the hinges to the upper and lower frame components of each of the first and second strut assemblies. The second strut assembly includes a hinge 105 that may include a plurality of different flexion stops to limit the flexion of the hinge, as seen in FIGS. 7 and 8. The hinge 103 of the first strut assembly may likewise include a plurality of flexion stops that can be set at the same angle as flexion stops of the second hinge 105. The flexion stops may be of a type known in the art of hinges in orthopedic devices.

Because the second strut assembly 104 is removable, it can provide flexion control for those users who need it. The second strut assembly can be added or removed with no effect of the unloading function of the force straps 116, 118. Its structure does not complicate donning or doffing of the device.

Referring to the embodiment of FIGS. 11 and 12, the suspension straps are secured to the second strut assembly by a fastener element such as a pin 136 extending from each of the upper and lower frame components. The suspension straps 120, 122 each include a plurality of holes 138 along at least a portion of the length of the straps and sized and configured for receiving the pin 136. The pin 136 defines an upper flange 140 arranged for securing to the suspension straps and preventing slippage of the suspension straps from the upper and lower frame components. The upper flange 140 extends at least over a portion of the suspension strap at the corresponding hole to which it is secured.

The upper and lower frame components 112, 114 define slots 139, 141 through which the suspension straps 120, 122 extend. When combined with the pin 136, the suspension straps are fully retained in both position and from slippage relative to the second strut assembly. The pin 136 may be rotatable to be more easily engageable or disengageable from the suspension strap.

Figure 14:
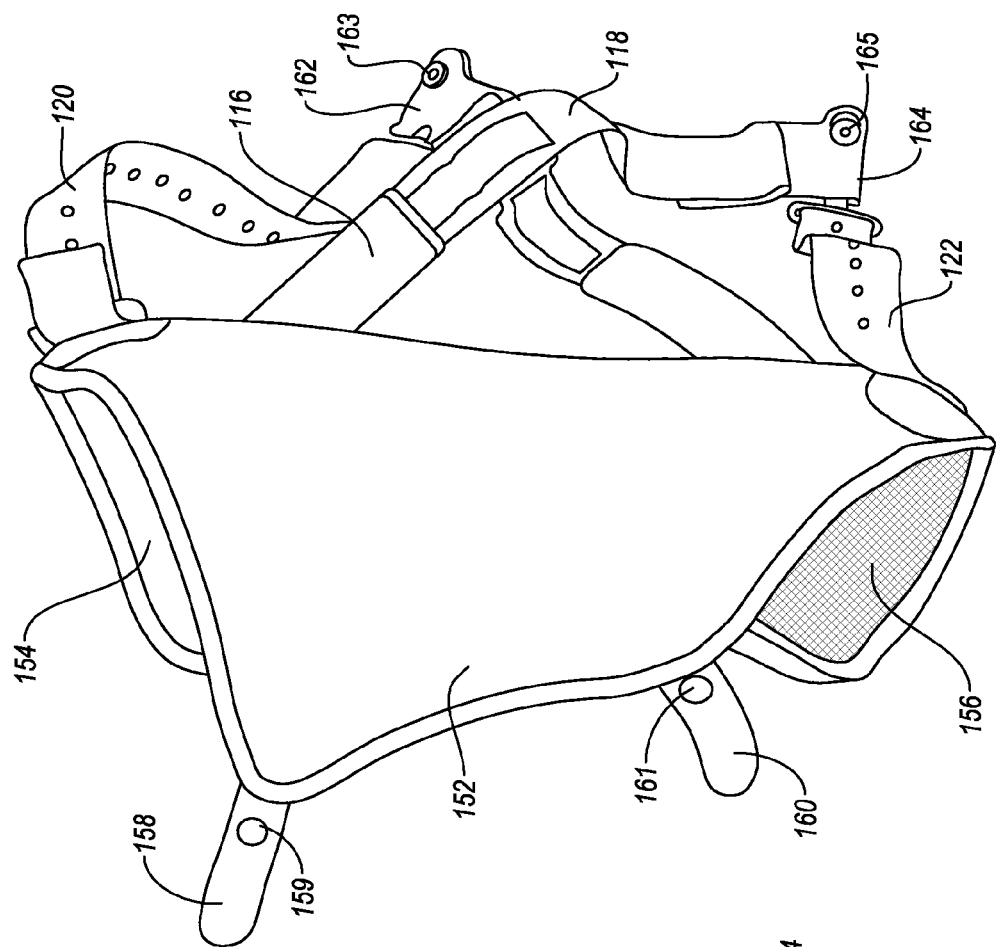
FIG. 14 is a perspective view of the liner sleeve of FIG. 13 in another open configuration from the inside of the orthopedic device.
Figure 13:
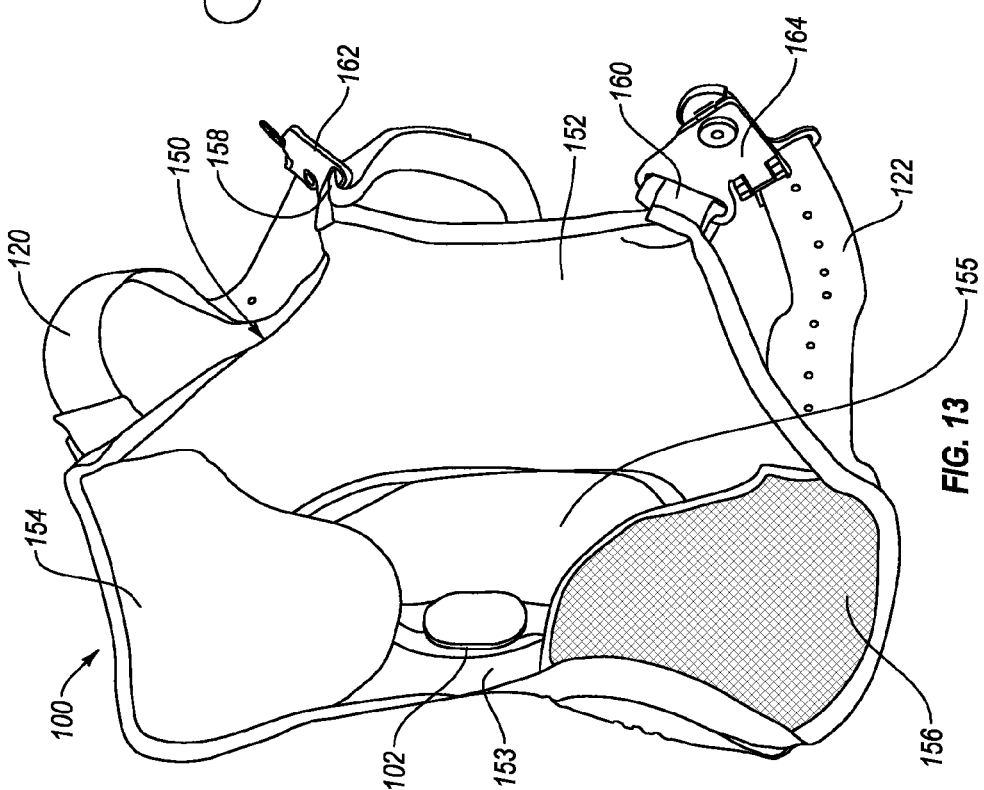
FIG. 13 is a perspective view of a liner sleeve for use with the orthopedic device of FIG. 7 and shown in an open configuration from the inside of the orthopedic device.
Figure 15:
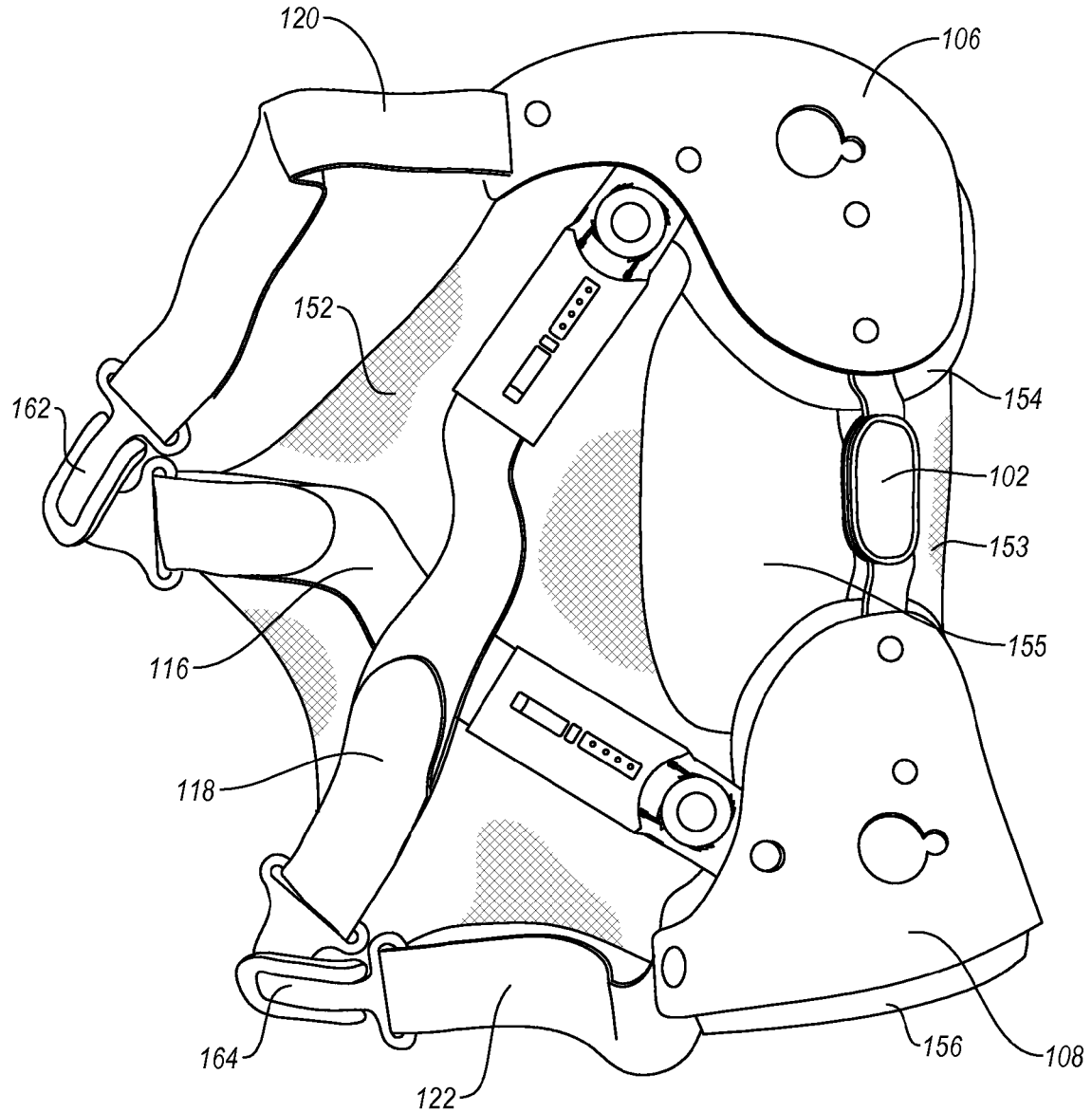
FIG. 15 is another perspective view of the liner sleeve of FIG. 13 in an open configuration from the outside of the orthopedic device.

Turning to the embodiment of FIGS. 13-15, a liner sleeve 150 includes a main panel 152, a side panel 153, and upper and lower liners 154, 156. Unlike the liner sleeve in the embodiment of FIGS. 7 and 8, which forms a continuously circumferential liner sleeve generally without interruption, the liner sleeve around liner sleeve 150 of the embodiment of FIGS. 13-15 opens to assist in the donning and doffing of the orthopedic device.

The main and side panels may formed from a flexible, elastic and breathable fabric, such as a combination of nylon and spandex. The side panel preferably is arranged to extend adjacent or near the hinge assembly, whereas the main panel is intended to generally wrap about a user's leg. The main and side panels are preferably stitched or otherwise secured to the upper and lower liners so the liner sleeve can be easily removed and adjusted.

The liners may be include padded and/or a frictional surface. The liners may be of any type described in U.S. Pat. No. 7,198,610, particularly as the spacer elements. In the embodiment of FIG. 13, the lower liner includes a padded layer that may include a foam core with covering layers, preferably with an outer layer intended to be adjacent the lower shell and an inner layer with a three-dimensional knit material having a frictional coating, such as silicone. The upper liner may be similarly constructed however without the frictional coating and instead a soft surface. The liners are preferably secured to the main panel and correspond to the upper and lower frame components by the connection of their hook-receivable layer to hook elements connected to or formed by the frame elements.

The liner sleeve may define an anterior opening 155 allowing for exposure of a user's knee at incision sites, which reduces or prevents irritation and interference from bandaging. The opening of the liner sleeve at the knee, which would otherwise undergo the greatest tension in material of the sleeve, improves the fit and decreases bunching of the sleeve. The opening remains open whether the straps of the orthopedic device are in the open or closed configuration.

According to the variation of FIGS. 13-15, and further in view of FIG. 16, the liner sleeve 150 includes upper and lower tabs 158, 160 secured to upper and lower buckle assemblies 162, 164. Preferably the various straps of the orthopedic device extend over the liner sleeve.

The tabs 158, 160 may include indicia 159 having markings or color corresponding to the correct buckle assemblies 162, 164, having similar indicia 163, 165. Once the tabs are secured to the buckle assemblies, the user can don and doff the orthopedic device 100 repeatedly without further steps since the liner sleeve is tied similarly to the buckle assemblies as with the force straps and the suspension straps.

FIG. 16 shows how the tabs secure to the force straps and are similarly oriented to correspond to the orientation of the force straps. The buckle assemblies define a slot 161 through which the tabs may extend or alternatively the tabs may secure directly onto one of the force straps or suspension straps similarly connected to the buckle assemblies. When the buckle assemblies secure to the upper and lower frame components, the liner sleeve 150 wraps within the orthopedic device, as understood by FIG. 14. The force straps and suspension straps are secured over the liner sleeve.

In the embodiments, the liner sleeve, whether circumferential or a wrap-around configuration, creates a full liner sleeve that can serve as a barrier between the straps and the skin of the user since the user may be sensitive to excessive flexion of the knee and the force applied by the straps. In the configuration of the wrap-around liner sleeve, the liner sleeve can easily provide access to a clinician for inspection of incision sites and observation for inspection by way of the facile method of opening and the anterior opening. Because the wrap-around liner sleeve is removable, it can be replaced if soiled or washed. The user can completely remove the liner sleeve if its use is no longer desired.

FIG. 17 shows a variation of attachment means for attaching the wrap-around liner sleeve to the upper and lower frame components. In this variation, the tabs (not shown) are secured to a keyhole clip 166 having a keyhole configuration including a larger lower opening 167 and a smaller upper opening 169 merged together. The frame component includes a pin 168 arranged to extend through the lower opening 167 and slip and secure into the upper opening 169 once the clip 166 is pulled away from the frame component. The clip 166 may include openings 170 to which the tabs of the sleeve may be stitched.

Figure 18:
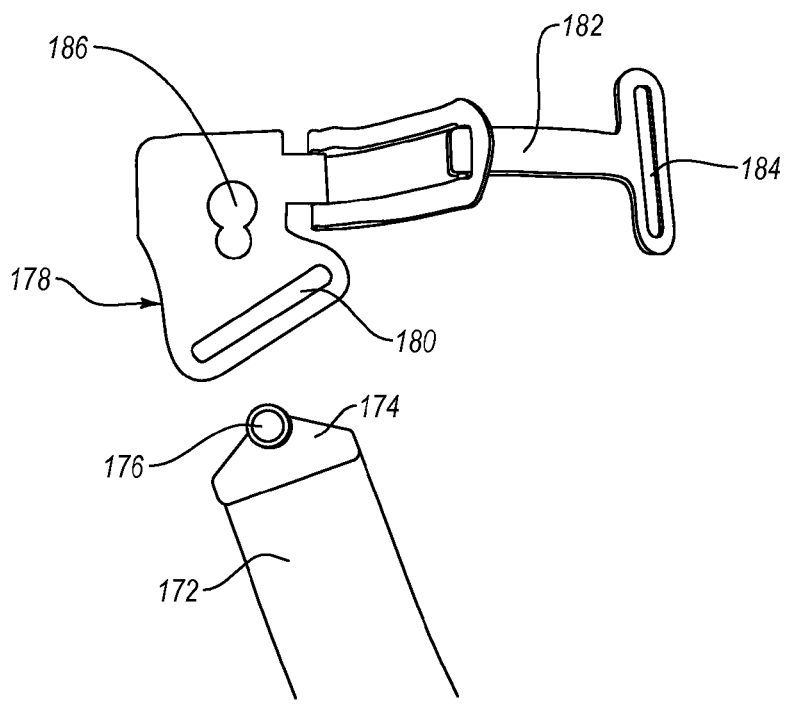
FIG. 18 is a detailed sectional view showing another variation of a strap tab for attachment to the orthopedic device of FIG. 7.

FIG. 18 exemplifies another variation of attachment means for attaching the wrap-around liner sleeve to the upper and lower frame components. This variation includes a tab 172 having a coupling member 174 at an end and forming a pin 176. The pin 176 is adapted to lock to a keyhole opening 186 formed similarly to the keyhole of the variation of FIG. 16, and defined by a buckle assembly 178. The buckle assembly 178 includes a first slot 180 for receiving a force strap (not shown) and a latch assembly 182 including a slot 184 for securing to a suspension strap (not shown). Much like the embodiment of FIG. 16, this variation allows the tabs of the liner sleeve to be secured to the buckle assembly so the liner sleeve opens when the force straps and suspension straps are disengaged from the frame components upon release of the buckle assembly.

For applying the orthopedic device of FIGS. 7 and 8 and variations, the initial application of the device includes placing the device on the user's leg, rotating the device 180 degrees so the hinge can bend with the ankle. The device is pulled over the ankle, and rotated back 180 degrees so the hinge is on the correct side. The device is pulled up the leg and the center of the hinge is aligned at the mid patella and the midline of anterior/posterior plane of the knee. The buckle assemblies are placed at respective locations on the upper and lower frame assemblies, and matched according to indicia, as explained above. The force and suspension straps are adjusted by trimming and attaching to the buckle assemblies accordingly.

FIG. 19 shows a variation of the upper and lower frame components or shells 106, 108. The shells include each may include regions having different thickness in order provide sufficient structural support while adding the requisite flexibility to closely embrace the leg depending on any volume changes.

At least one of the shells 106, 108 may have a thickened region 175, 179 corresponding to a side portion upon which a strut and hinge assembly secures to the frames 106, 108. A thinned anterior region 171, 177 preferably extends from the thickened region 175, 179, such as over the anterior upper and lower leg portions. A thinned peripheral region 173 may surround the thickened region 175, 179, and may either be thicker or thinner than the thinned anterior region 171, 177. A tapering thickness region 183 may be formed between the thickened and thinned regions to serve as a transition in thickness to minimize stress points and surfaces that may catch. The lower shell 108 may include both anterior and posterior thinned regions 177, 185 extending from the thickened region 179. Elongate or otherwise shaped openings 187 may be formed through either of the shells 106, 108 and arranged to facilitate bending.

The shells 106, 108 are preferably formed from the same material and the thinned and thickened regions are continuously formed without interruption of the same material or from region to region. An example is that each shell may be injection molded by a polymeric material and formed in a same mold having both the thickened and thinned regions. The injection molded shells can includes a plurality of different slots, channels, keyholes and such for attachment of straps, flexion control kit, liner sleeve and other features to the brace.

The thinned anterior region 171 may include a slot 191 at a free end portion for receiving a corresponding suspension strap. In this manner, rather than using a buckle or strap tab, the slot 179 reduces pivoting of the free end portion of the shell due to the suspension strap, especially with the upper or thigh shell. The thinned anterior region 171 with the slot allows the suspension strap to tightly secure against the thigh of a user to allow the shell at least at the thinned anterior region 171 to closely follow the contour of a user's leg through volume changes. The lower shell 108 represents how a keyhole 189 can be similarly formed at an end portion of the shell to encourage bending of the thinned anterior region 177.

While discussed in the context of a knee brace, the components of the device can be extended to other bracing needs such as for an elbow, ankle, wrist, and other anatomical complications and associated rehabilitation.

Various methods may use the orthopedic device during rehabilitation phases. The methods may include applying and maintaining a force with the strap on a knee at a side of a knee opposite repairing cartilage, maintaining a selected range of motion of the knee by a range of motion hinge of the orthopedic device by adjusting flexion and extension stops on the range of motion hinge, providing stability to the knee by lateral stability straps connected to the orthopedic device and circumferentially extending at locations adjacent above and below the knee.

The method may also include steps of permanently securing the first hinge assembly to the first and second portions, and detachably mounting the second hinge assembly to the first and second portions after certain rehabilitation phases are completed.

The invention claimed is:

1. An orthopedic device, comprising:
   a frame including first and second frame portions;
   a first strut assembly permanently secured to and connecting the first and second frame portions and including a hinge located between the first and second frame portions;
   a second strut assembly detachably connected to the first and second frame portions, the second strut assembly having upper and lower frame components connected to one another by a hinge;
   a force strap arranged to spiral between and connect to the first and second frame portions, the force strap including a first end connecting to a buckle assembly removably securing to one of the first and second frame portions;
   a suspension strap connecting to opposed sides of at least one of the first and second frame portions, the suspension strap including a first end connecting to the buckle assembly;
   a stability strap arranged to generally form a circumferential loop about the first and second strut assemblies;
   wherein the second strut assembly detachably secures to the suspension strap and extends through at least one slot formed by at least one of the upper and lower frame portions, the force strap extends under the second strut assembly such that the second strut assembly can be added or removed with no effect of the unloading function of the force straps.

2. The orthopedic device according to claim 1, wherein the second strut assembly includes a fastener element directly securable to the suspension strap.

3. The orthopedic device according to claim 2, wherein the fastener element is a pin extending from at least one of the upper and lower frame components (and between first and second slots of the at least one slot of at least one of the upper and lower frame components, the suspension strap defines a plurality of holes sized and configured for receiving the pin.

4. The orthopedic device according to claim 3, wherein the pin defines an upper flange arranged for securing to the suspension strap thereby preventing slippage of the suspension strap from one of the upper and lower frame components.

5. The orthopedic device according to claim 1, wherein the second strut assembly includes first and second struts connected to one another by a hinge, the second strut assembly further including a support mounted at and extending from a first end of the first strut.

6. The orthopedic device according to claim 1, wherein the suspension strap is secured at or adjacent a first end portion of the first and second strut assemblies, and the stability strap is mounted below the first end portion of the first and second strut assemblies.

7. The orthopedic device according to claim 1, wherein the first and second strut assemblies define at least one retainer arranged to maintain the stability strap in a lateral position relative to the first and second strut assemblies.

8. The orthopedic device according to claim 7, wherein the retainer is a loop formed along at least the second strut assembly.

9. The orthopedic device according to claim 1, wherein the suspension strap and the stability strap extend over the first and second strut assemblies.

10. The orthopedic device according to claim 1, further comprising first and second suspension straps connecting to opposed sides of at least one of the first and second frame portions, respectively, wherein the second strut assembly defines first and second ends detachably securing to the first and second suspension straps, respectively.

11. The orthopedic device according to claim 1, wherein the second strut assembly includes a range of motion hinge including at least one of flexion and extension stops.

12. The orthopedic device according to claim 1, further comprising a liner sleeve extending the length of and connecting to the first and second strut assemblies.

13. The orthopedic device according to claim 1, further comprising a liner sleeve having an attachment element securing to the suspension strap and enabling opening and closing of the liner sleeve based on connection of the suspension strap relative to the upper and lower frame portions.

14. An orthopedic device, comprising:
   a frame including first and second frame portions;
   a first strut assembly permanently secured to and connecting the first and second frame portions and including a hinge located between the first and second frame portions;
   a second strut assembly detachably connected to the first and second frame portions, the second strut assembly having upper and lower frame components connected to one another by a hinge;
   a force strap arranged to spiral between and connect to the first and second frame portions, the force strap including a first end connecting to a buckle assembly removably securing to one of the first and second frame portions;
   first and second suspension straps connecting to opposed sides of at least one of the first and second frame portions, respectively, wherein the second strut assembly defines first and second ends detachably securing to the first and second suspension straps, respectively;
   characterized in that the second strut assembly detachably secures to at least one of the first and second suspension straps and extends through at least one slot formed by at least one of the upper and lower frame portions, the force strap extends under the second strut assembly such that the second strut assembly can be added or removed with no effect of the unloading function of the force straps.

15. An orthopedic device, comprising:
   a frame including first and second frame portions;
   a first strut assembly permanently secured to and connecting the first and second frame portions and including a hinge located between the first and second frame portions;
   a second strut assembly detachably connected to the first and second frame portions, the second strut assembly having upper and lower frame components connected to one another by a hinge, the second strut assembly including a range of motion hinge including at least one of flexion and extension stops;

a force strap arranged to spiral between and connect to the first and second frame portions, the force strap including a first end connecting to a buckle assembly removably securing to one of the first and second frame portions;

a suspension strap connecting to opposed sides of at least one of the first and second frame portions, the suspension strap including a first end connecting to the buckle assembly;

characterized in that the second strut assembly detachably secures to the suspension strap and extends through at least one slot formed by at least one of the upper and lower frame portions, the force strap extends under the second strut assembly such that the second strut assembly can be added or removed with no effect of the unloading function of the force straps.

16. An orthopedic device, comprising:

a frame including first and second frame portions;

a first strut assembly permanently secured to and connecting the first and second frame portions and including a hinge located between the first and second frame portions;

a second strut assembly detachably connected to the first and second frame portions, the second strut assembly having upper and lower frame components connected to one another by a hinge;

a force strap arranged to spiral between and connect to the first and second frame portions, the force strap including a first end connecting to a buckle assembly removably securing to one of the first and second frame portions;

a suspension strap connecting to opposed sides of at least one of the first and second frame portions, the suspension strap including a first end connecting to the buckle assembly;

characterized in that the second strut assembly detachably secures to the suspension strap and extends through at least one slot formed by at least one of the upper and lower frame portions, the force strap extends under the second strut assembly such that the second strut assembly can be added or removed with no effect of the unloading function of the force straps;

further comprising a liner sleeve extending the length of and connecting to the first and second strut assemblies.

* * * * *